United States Patent
Stevens et al.

(10) Patent No.: US 6,365,756 B1
(45) Date of Patent: Apr. 2, 2002

(54) PROCESS FOR THE PRODUCTION OF OPTICALLY ENRICHED (R)- OR (S)-ALBUTEROL

(75) Inventors: Anne Stevens, Tokai; Roger Hunter, Claremont; Luigi Nassimbeni, Rosebank; Mino Caira, Claremont, all of (ZA); Janet Scott, South Yarra (AU); Rainer Clauss, Twickenham (GB); Joanne Gibson, Cape Town; Tarron Grimmbacher, Claremont, both of (ZA)

(73) Assignee: Fine Chemical Corporation Limited, Cape Town (ZA)

( * ) Notice: Subject to any disclaimer, the term of this patent is extended or adjusted under 35 U.S.C. 154(b) by 0 days.

(21) Appl. No.: 09/622,946

(22) PCT Filed: Feb. 19, 1999

(86) PCT No.: PCT/GB99/00518

§ 371 Date: Nov. 13, 2000

§ 102(e) Date: Nov. 13, 2000

(87) PCT Pub. No.: WO99/42460

PCT Pub. Date: Aug. 26, 1999

(30) Foreign Application Priority Data

Feb. 20, 1998 (ZA) .............................................. 98/1428

(51) Int. Cl.$^7$ ........................ C07D 319/02; C07B 57/00
(52) U.S. Cl. ...................................... 549/365; 564/303
(58) Field of Search ............................ 549/365; 564/303

(56) References Cited

U.S. PATENT DOCUMENTS

| 5,399,765 | A | * | 3/1995 | Gao et al. .................... 564/365 |
| 5,545,745 | A | * | 8/1996 | Gao et al. ..................... 560/42 |
| 5,958,456 | A | * | 9/1999 | Baichwal et al. ........... 424/489 |
| 6,083,993 | A | * | 7/2000 | Barberich et al. .......... 514/649 |
| 6,235,927 | B1 | * | 5/2001 | Vries et al. ................. 562/401 |

FOREIGN PATENT DOCUMENTS

| DE | 23 10 142 | 9/1974 |
| WO | WO 95/32178 | 11/1995 |

* cited by examiner

Primary Examiner—Deborah C. Lambkin
(74) Attorney, Agent, or Firm—Pillsbury Winthrop LLP

(57) ABSTRACT

A process for the production of optically enriched (R)- or (S)-albuterol or (R)- or (S)-albuterol salts by the resolution of a novel ketal derivative 2-(N-t-butylamino)-1-(+2,2-dimethyl-1,2-benzodioxin-6-yl) ethanol, with a chiral tartaric acid derivative.

10 Claims, 4 Drawing Sheets

PROCESS FOR THE PRODUCTION OF OPTICALLY ENRICHED (R)- OR (S)-ALBUTEROL

BACKGROUND OF THE INVENTION

This invention relates to a process for the production of optically enriched (R)- or (S)-albuterol or (R)- or (S)-albuterol salts, by the resolution of a novel ketal derivative of the enantiomers of albuterol, with a chiral tartaric acid derivative.

Albuterol, 2-(N-t-butylamino)-1-(4-hydroxy-3-hydroxymethylphenyl) ethanol, (1), is a β-2 agonist with bronchodilatory action. It is widely used, as a racemic mixture, in the treatment of asthma.[1,2,3]

Of the two possible optical isomers the (R)-enantiomer is reported to be significantly more potent with respect to β-2 agonist activity than the (S)-enantiomer.[4]

A number of methods for producing optically enriched albuterol have been described. These include resolution of a mixture of enantiomers of 5-[2-[(1,1-dimethylethyl)amino]-1-hydroxyethyl]-2-hydroxybenzoate[5] or 5-[2-[(1.1-dimethylethyl)amino]-1-hydroxyethyl]-2-(phenylmethoxy) benzoate[6] and enantioselective reduction of an α-iminoketone to an α-amino alcohol using a borane reducing agent and a chiral 1,3,2-oxazaborole catalyst.[7]

SUMMARY OF THE INVENTION

According to a first aspect of the invention there is provided a process for the preparation of a compound of the formula (2)

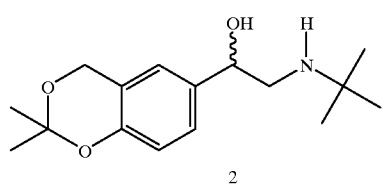

(2)

viz. 2-(N-t-butylamino)-1-(2,2-dimethyl-1,2-benzodioxin-6-yl) ethanol, which is a novel ketal derivative of albuterol, which process includes the steps of:

(1) suspending a compound of the formula (1) (which is albuterol)

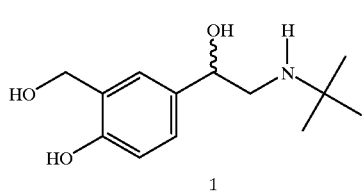

(1)

or a salt thereof, in acetone;

(2) adding to the mixture of step (1) a suitable acid with stirring to form the compound of the formula (2);

(3) adding to the mixture of step (2) a suitable aqueous or non-aqueous basic solution; and (4) recovering the compound of the formula (2) from the mixture of step (3).

Thereafter, the compound of the formula (2) in crude form may be recrystallised from a suitable solvent, or purified using column chromatography, to yield pure crystalline compound of the formula (2).

When the compound of the formula (1) is a racemic mixture, then the, compound of the formula (2) is also produced as a racemic mixture.

According to a second aspect of the invention there is provided a process for the optical resolution of a mixture of enantiomers of a compound of the formula (2) above, into its (R)-isomer designated (R)-2 and its (S)-isomer designated (S)-2, which process includes the steps of:

(i) reacting the mixture of enantiomers of the compound of the formula (2), dissolved in a suitable solvent, with an enantiopure tartaric acid derivative such as (2S,3S)-(+)-di-O-benzoyl tartaric acid (3a), (2S,3S)-(+)-di-O-(p-toluoyl)-tartaric acid (4a), (2R,3R)-(−)-di-O-benzoyl tartaric acid (3b), or (2R,3R)-(-)-di-O-(p-toluoyl)-tartaric acid (4b), or the like;

(ii) precipitating selectively out of the solution of step (i) a compound of the formula:
(R)-2:tartaric acid derivative salt or
(S)-2:tartaric acid derivative salt;

(iii) suspending the (R)-2:tartaric acid derivative salt or the (S)-2: tartaric acid derivative salt in a suitable organic solvent and stirring to improve optical purity, and then recovering the (R)-2:tartaric acid derivative salt or the (S)-2:tartaric acid derivative salt by filtration;

(iv) adding the (R)-2:tartaric acid derivative salt or the (S)-2:tartaric acid derivative salt from step (iii) to a mixture of an aqueous solution of a base and a suitable organic solvent; and (v) recovering the compound (R)-2 or the compound (S)-2 from the organic phase of step (iv).

According to a third aspect of the invention there is provided a process for the hydrolysis of a compound of the formula (2) to give a compound of the formula (1) either as the free base or as a salt, which includes the steps of:

(a) dissolving the compound of the formula (2), either enantiomerically enriched or as the racemic mixture, in an excess of an acid, and water or any suitable organic solvent, to hydrolyse the compound of the formula (2); and (b) recovering the compound of the formula (1) either as a salt of the acid used in step (a), or as the free base.

Thereafter the compound of the formula (1) or a salt thereof, in crude form, may be purified, for example by recrystallisation from a suitable solvent system.

When the starting compound of the formula (2) is enantiomerically enriched, then the resulting compound of the formula (1) is also enantiomerically enriched. This provides a method for resolving the enantiomers of albuterol into the (R)-enantiomer and the (S)-enantiomer.

According to a fourth aspect of the invention there is provided a process for the racemisation of optically enriched compound of the formula (1) or a salt thereof or optically enriched compound of the formula (2) or a salt thereof, to give a mixture of enantiomers of the compound of the formula (1), which process includes the steps of:

(A) dissolving optically enriched compound of the formula (1) (i.e either the (R)-isomer designated (R)-1 or the (S)-isomer designated (S)-1) or a salt thereof, or optically enriched compound of the formula (2) (i.e either the (R)-isomer designated (R)-2 or the (S)-isomer designated (S)-2, in a solution of an excess of a suitable acid and a suitable solvent to produce racemised compound of the formula (1);

(B) adding to the solution of step (A) a suitable aqueous or non-aqueous base; and (C) recovering a mixture of enantiomers of the compound of the formula (1) from the mixture of step (B).

This process provides a means for recycling the undesired enantiomer of compound of the formula (1) to produce more of the desired enantiomer. The mixture of enantiomers of the compound of the formula (1) which is produced may be derivatised, resolved and hydrolysed according to the processes described under aspects one to three of the invention, to obtain the compound of the formula (2) and hence the compound of the formula (1) enriched in the desired optical isomer.

DESCRIPTION OF EMBODIMENTS

Figure 1:
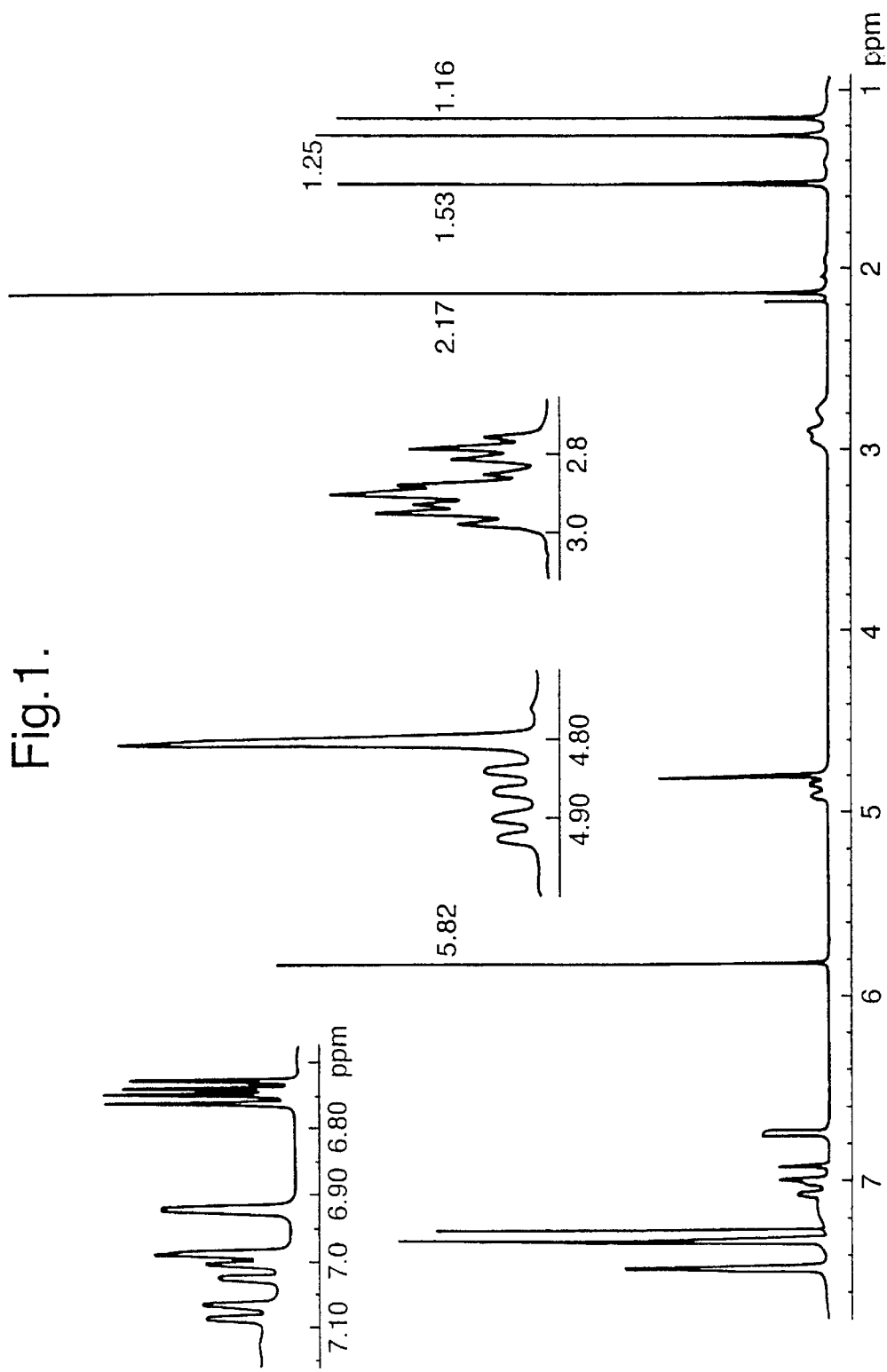
FIG. 1 is a $^1$H-NMR spectrum of (rac)-2 with (R)-O-acetyl mandelic acid in CDCl$_3$.

The present invention encompasses four processes:

(1) A process for the preparation of compound (2), i.e a ketal derivative of compound (1), which is albuterol.
(2) A process for the optical resolution of a mixture of enantiomers of compound (2) into its (R)-isomer and its (S)-isomer.
(3) A process for the hydrolysis of compound (2) and enantiomerically enriched compound (2) to give compound (1) or enantiomerically enriched compound (1).
(4) A process for the racemisation of optically enriched compound (1) or compound (2) to give a mixture of enantiomers of compound (1).

When these four processes are combined, there is provided a process for producing optically enriched albuterol or albuterol salts with enantiomeric excesses greater than 99% achievable, as well as a process whereby the undesired isomer of albuterol may be racemised and recycled to achieve a higher yield of the desired isomer of albuterol.

The designations (R)-1, (S)-1, (R)-2 and (S)-2 and their respective salts used herein refer to enantiomerically enriched compounds usually of 90% ee or greater, unless otherwise stated.

The four processes of the invention are described in more detail below.

A Ketalisation

In the first process of the invention, a mixture of enantiomers of compound (1) or a salt thereof is condensed with acetone in the presence of an acid and, if required, a dehydrating agent, which may be added simultaneously with or after the acid, to form compound (2), See Scheme 1. Preferable acid/dehydrating agent systems include sulfuric acid; sulfuric acid and anhydrous copper sulphate; and boron trifluoride diethyl etherate. The acid is preferably present in an amount of between 1 to 5 molar equivalents and the reaction is preferably cooled to a temperature of between −15° C. to 10° C.

Scheme 1:

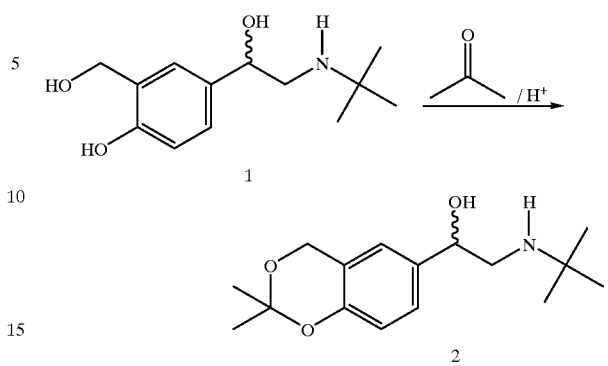

Acetone, which has the formula:

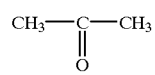

is utilised both as a solvent and a reagent.

Compound (2) is isolated from the reaction mixture after neutralisation of the excess acid with a suitable base, such as sodium hydroxide (NaOH), potassium hydroxide (KOH), or sodium carbonate (Na$_2$CO$_3$) dissolved in either water or a mixture of water and a lower alcohol, giving an aqueous basic solution, or a lower alcohol, giving a non-aqueous basic solution. The lower alcohol may be methanol.

When an aqueous basic solution is used, the acetone is removed under reduced pressure and compound (2) is extracted into a suitable organic solvent such as ethyl acetate, chloroform, toluene or any other water non-miscible solvent in which compound (2) is soluble. The organic phase is then dried over anhydrous Na$_2$SO$_4$, filtered and the solvent removed under reduced pressure.

When a non-aqueous basic solution is used, compound (2) is recovered after filtration of solids and removal of solvent under reduced pressure. The crude compound (2) may then be purified by dissolving it in a suitable organic solvent, such as ethyl acetate, chloroform or toluene and washing the organic phase with water.

Further purification of compound (2) may be performed, for example by recrystallisation from suitable solvents such as acetonitrile, methyl ethyl ketone or acetone or a mixture of the organic solvent and water, or by column chromatography.

B Resolution and liberation of ketal

The second process of the invention is a process for the optical resolution of a mixture of enantiomers of compound (2) into its (R)-isomer designated (R)-2 and its (S)-isomer designated (S)-2 which have the formulae:

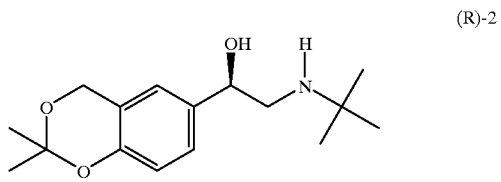

(R)-2

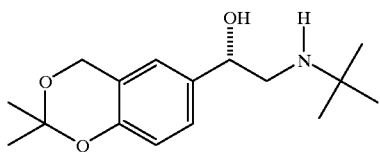
(S)-2

In terms of this process, compound (2) as a mixture of enantiomers, is dissolved in a suitable solvent, preferably a lower alcohol such as methanol or ethanol, and a solution of the resolving agent, a chiral tartaric acid derivative such as that of the formulae (3a), (3b), (4a) or (4b), in the chosen solvent, is added. One isomer of compound (2) selectively crystallises from solution as a salt of the tartaric acid derivative used.

When the chiral acid used is a compound of the formulae (3a) or (4a):

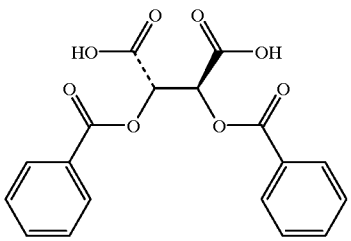
(3a)

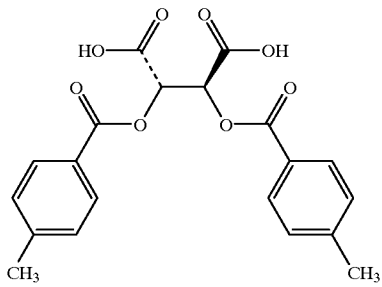
(4a)

i.e. either (2S,3S)-(+)-di-O-benzoyl tartaric acid (3a), or (2S,3S)-(+)-di-O-(p-toluoyl)-tartaric acid (4a), then there is precipitated out a salt of the formula 2(R)-2:3a i.e a salt of (R)-2 and (3a) in a ratio of 2:1, or of the formula 2(R)-2:4a i.e a salt of (R)-2 and (4a) in a ratio of 2:1; and the optically enriched compound (R)-2 may be liberated by treatment with a base.

When the chiral acid used is a compound of the formulae (3b) or (4b):

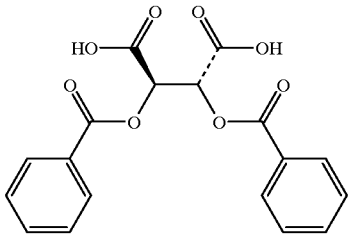
(3b)

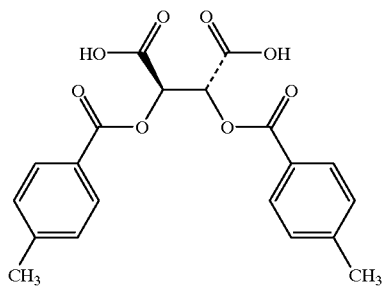
(4b)

i.e (2R,3R)-(−)-di-O-benzoyl tartaric acid (3b)

or (2R,3R)-(−)-di-O-(p-toluoyl)-tartaric acid (4b), then there is precipitated out a salt of the formula 2(S)-2:3b i.e a salt of (S)-2 and (3b) in a ratio of 2:1, or of the formula 2(S)-2:4b i.e a salt of (S)-2 and (4b) in a ratio of 2:1; and the optically enriched compound (S)-2 may be liberated by treatment with a base.

The ratios of the resolving agent to the ketal, i.e compound (2), may be in the range of from 0.5 to 1 mole equivalents inclusive, and the solutions may be combined hot or may be mixed at ambient temperature. The solution (if hot) is allowed to cool, with or without stirring, to ambient temperature, and may be chilled to facilitate crystallisation. Solvent volumes may be reduced by distillation, either under reduced pressure or at ambient pressure, to increase the yield of salt. The salt is recovered by filtration, dried and the degree of enrichment of the desired enantiomer of compound (2) determined by measurement of optical rotation or HPLC using a suitable chiral column.

The salts 2(R)-2:3a, 2(R)-2:4a, 2(S)-2:3b, or 2(S)-2:4b, may be further purified by slurry of the crude salt in a suitable solvent such as a lower alcohol, e.g methanol or ethanol. The mixture is stirred to improve optical purity, and the relevant salt is then recovered by filtration. This step may be repeated, if necessary, further to improve optical purity.

Recovery of the resolved compound (2) is achieved by dissociation of the salt in a vigorously stirred mixture of an aqueous solution of a suitable base such as sodium carbonate, or sodium hydroxide, and a suitable organic solvent such as ethyl acetate, toluene or chloroform, into which compound (2) is extracted. The phases are separated, the organic phase dried over a suitable dehydrating agent such as anhydrous $Na_2SO_4$ or $MgSO_4$, and the organic solvent is removed under reduced pressure to yield optically enriched compound (2).

Optical purity of compound (2) may be determined by NMR assay, using a suitable chiral shift reagent such as O-acetylmandelic acid, by measurement of optical rotation or, preferably, by HPLC analysis using a suitable chiral column. Optical purity may be enhanced by recrystallisation of the optically enriched compound (2) from a suitable solvent such as acetonitrile, acetone or methyl ethyl ketone or a mixture of the chosen organic solvent and water.

C Hydrolysis of ketal

The third process of the invention is a process for the hydrolysis of compound (2). In terms of this process, preferably optically enriched compound (2) is hydrolysed to yield optically enriched compound (1), i.e albuterol or a salt thereof.

This may be achieved by dissolution of compound (2) in a solution of a suitable acid such as acetic acid, sulfuric acid, hydrochloric acid, trifluoroacetic acid, toluenesulfonic acid or camphorsulfonic acid, in water or other suitable solvents, including lower alcohols, acetonitrile and tetrahydrofuran, or a mixture of water and an organic solvent. The reaction is carried out at a temperature of between 0° C. and reflux temperature, preferably between 20° C. and reflux temperature and with greater than 1 up to 5 molar equivalents of a strong acid such as a mineral acid, or up to 30 molar equivalents of a weaker acid such as acetic acid. Depending on the temperature, acid and solvent used, the hydrolysis is carried out for between 10 minutes and 6 hours. Under these conditions the enantiomeric excess did not change significantly.

In the case of an aqueous process, when an inorganic acid is used, once hydrolysis is complete, the excess acid is neutralised with a suitable base, such as NaOH or $Na_2CO_3$ to pH of ca 3.5 and the solvent removed under reduced pressure. The residue may then be neutralised further using the preferred base to a pH of ca 10 in a suitable organic solvent, preferably a lower alcohol, the solids filtered off and the solvent removed under reduced pressure to give compound (1) in crude form as its free base.

In the case of a non-aqueous hydrolysis, once hydrolysis is complete, the excess acid is neutralised with a suitable base, such as NaOH or $Na_2CO_3$ to a pH of ca 10, the solids filtered off and the solvent removed under reduced pressure to give compound (1) in crude form as its free base.

Alternatively, in order to isolate compound (1) as a salt, for example as an acetate salt, solvent and excess acid may be removed under reduced pressure and the resulting salt of optically enriched compound (1) isolated by crystallisation from a suitable solvent system such as methanol/ethyl acetate. In the case of an inorganic acid such as HCl or $H_2SO_4$ being used for the hydrolysis, the n the salt of compound (1) may be isolated by partial neutralisation with an organic base, such as triethylamine, and allowed to crystallise in a reduced volume of solvent.

(R)-1 or (S)-1 in crude form as its free base, may be purified by recrystallisation from solvent systems such as methanol, ethanol, methanol/ethyl acetate, ethanol/ethyl acetate, ethyl acetate, isopropanol/ethyl acetate, acetone or tetrahydrofuran. Recrystallisation of optically enriched compound (1) may be used to improve the enantiomeric excess.

D Racemisation of optically enriched ketal

The fourth process of this invention is the racemisation of optically enriched compound (1), preferably as its derivative, compound (2), to give a mixture of enantiomers of compound (1).

In terms of this process optically enriched compound (2) is dissolved in a solution of an excess of an acid such as sulfuric acid, hydrochloric acid, acetic acid or trifluoroacetic acid, and water, or any suitable organic solvent, such as a lower alcohol, acetonitrile or tetrahydrofuran, or a mixture of water and an organic solvent. Water is by far the preferred solvent since it reduces byproduct formation. The amount of acid used may be from 5 to 50 molar equivalents inclusive. The reaction is preferably heated to between ca 0° C. and reflux temperature. Deprotection of compound (2) to compound (1) is rapid with excess acid and thereafter racemisation proceeds according to the mechanism of D. P. Venter.[8] The decrease in enantiomeric excess may be measured by optical rotation or by HPLC analysis using a suitable chiral column.

Once sufficient racemisation has been achieved, the solution is cooled and the excess acid neutralised with, preferably, an aqueous base such as NaOH or $Na_2CO_3$ to a pH of ca 3.5. The solvent is then removed under reduced pressure and the salt of compound (1) freed by addition of further base in a lower alcohol until a pH of ca 10 is obtained. The solids may then be filtered off and the filtrate concentrated under reduced pressure to give crude, racemised compound (1) as its free base.

Alternatively, in order to isolate racemised compound (1) as a salt, the excess acid may be neutralised, as above, to a pH of ca 3.5. The solvent may then be removed under reduced pressure to give crude compound (1) and salts of neutralisation. The mixture of the salt of compound (1) and the inorganic salts may then be slurried in acetone and ketalised directly, according to the first process of this invention.

EXAMPLES

General

Melting points were measured using a Reichert-Jung Thermovar hot-stage microscope and are uncorrected. Optical rotations were measured on a Perkin-Elmer 141 polarimeter. Microanalyses. were determined using a Fisons EA 1108 CHNS-O instrument. $^1$H-NMR spectra were recorded on a Varian VXR-200 (200 MHz) or a Varian Unity Spectrometer (400 MHz). $^{13}$C-NMR spectra were recorded on the same instruments at 50 or 100 MHz. The relevant solvent peak ($CHCl_3$ or DMSO) was used as an internal standard in each case. High performance liquid chromatography was performed on a Hewlett Packard 1090 system with a diode array detector and a Hewlett Packard 3393A integrator.

Thin layer chromatography was performed on aluminium backed silica gel 60 $F_{254}$ plates. The plates were visualised under ultraviolet light and by spraying with ceric ammonium sulphate in 8 mol.dm$^{-3}$ sulfuric acid and baking at 200° C. Column chromatography was conducted with Merck Kieselgel 60, 70–230 mesh.

Determination of Optical Purity (a) High Performance Liquid Chromatography

| Chiral HPLC column | Chirex (S)-ICA and (R)-NEA (phase 3022) with a suitable mobile phase system. |
|---|---|
| or | Chirobiotic Teicoplanin with a suitable mobile phase. |

The enantiomeric excesses were calculated using $$\% \, ee = 100 \times \left[ \frac{\text{Area}(R) - \text{Area}(S)}{\text{Area}(R) + \text{Area}(S)} \right]$$

(b) $^1$H-NMR

Typically compound (2) (5mg) and (R)- or (S)-O-acetylmandelic acid (6 mg) were dissolved in $CDCl_3$ (1 cm$^3$) and the $^1$H-NMR spectra recorded (400 MHz). Several of the protons in compound (2) gave well distinguished peaks for each diastereomer formed in solution and integration of these pairs (usually the t-Bu peaks) allowed determination of the optical purity.

Figure 2:
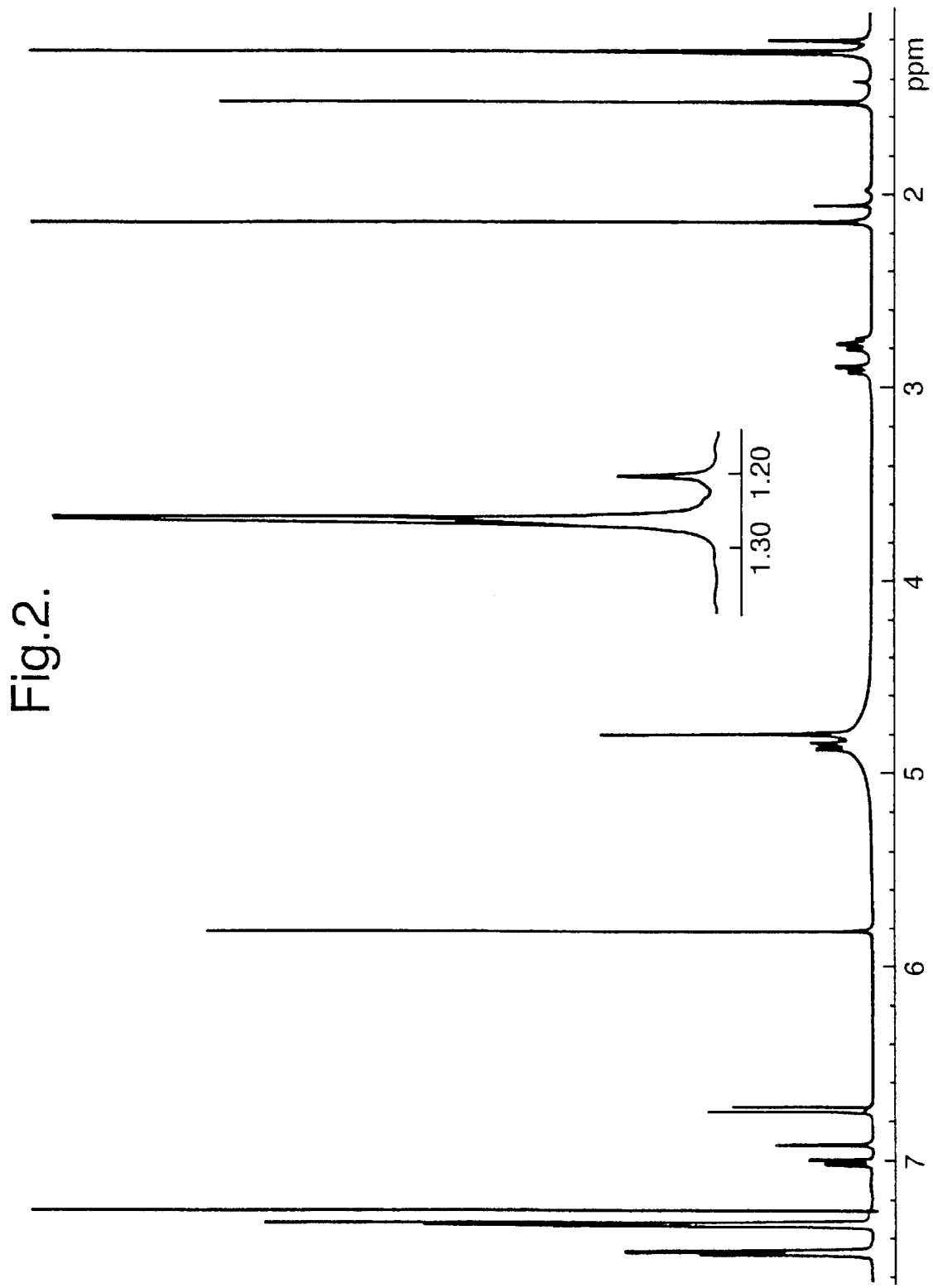
FIG. 2 is a $^1$H-NMR spectrum of (R)-2 with (R)-O-acetyl mandelic acid in CDCl$_3$.

Spectra obtained with (rac)-2 (racemic compound (2)) and (R)-2 respectively have been reproduced in FIGS. 1 and 2.

Hereinafter the compound of the formula (2) is referred to simply as 2.

Likewise the compounds of the formulae (1), (3a), (4a), (3b) and (4b) are simply referred to by number.

Confirmation of Absolute Configuration in 2

The (R)-phenylethyl urea of (+)-2 was prepared and the structure elucidated using X-ray crystallography. The absolute configuration at the chiral centre in (+)-2 was shown to be (S).

Example 1

Synthesis of (R,S)-2

Freshly distilled $BF_3OEt_2$, (2.7 cm³, 22.0 mmol) was added dropwise to a stirred mixture of (R,S)-albuterol ((R, S)-1) (2.39 g, 10.0 mmol) in dry acetone (50 cm³) under nitrogen in an ice bath. The solution was stirred at ca 0° C. for 60 minutes after which it was slowly poured into 50 cm³ cold aqueous $Na_2CO_3$. The excess acetone was removed under reduced pressure and the mixture extracted three times with an equal volume of ethyl acetate. The organic phase was dried ($MgSO_4$) and the solvent removed under reduced pressure to give a crystalline crude product (2.70 g). Column chromatography on silica gel with ethyl acetate/ petroleum ether (boiling range 60–80° C.)/triethylamine 50/45/5 afforded the white crystalline product (R,S)-2 (2.67 g, 9.57 mmol, 96%), mp 91–92° C. (acetone).

Example 2

Synthesis of (R,S)-2

(R,S)-Albuterol (9.56 g, 40 mmol) was suspended in acetone (150 ml) and cooled in an ice/water mixture at 0–5° C. Concentrated $H_2SO_4$ (6.9 ml, 120 mmol, 3 equiv.) was then added dropwise. 3,5 hours later anhydrous $CuSO_4$ (7.0 g, 40 mmol) was added. TLC monitoring of the reaction showed some starting material remaining unreacted. After a total of 5.5 hours a chilled solution of NaOH (10.0 g, 250 mmol, 2.1 equiv.) in methanol (75 ml) was added in a single portion and a blue-green slurry formed. The precipitate was removed by filtration through a bed of celite, washed with acetone and the filtrate concentrated under reduced pressure. The residue was re-dissolved in ethyl acetate (150 ml) and washed with water (2×100 ml) and brine (75 ml). The organic phase was dried over anhydrous $Na_2SO_4$, the drying agent filtered off, washed with ethyl acetate, and the filtrate concentrated under reduced pressure. The residue was taken up in toluene and re-concentrated under reduced pressure to give an off-white solid (R,S)-2 8.97 g (80%).

Example 3

Synthesis of (R,S)-2

(R-S)-Albuterol (4.78 g, 20 mmol) was suspended in acetone (100 ml) and cooled in an ice/water mixture to 0–5° C. Concentrated $H_2SO_4$ (2.3 ml, 40 mmol, 2 equiv.) was added dropwise. The reaction mixture, as monitored by TLC, still contained some starting material. After a total of 2.75 hours a chilled solution of NaOH (3.20 g, 80 mmol) in methanol (40 ml) was added in a single portion, followed by solid $K_2CO_3$ (400 mg, 3 mmol) and solid anhydrous $Na_2SO_4$. The mixture was filtered through a bed of celite, the solids washed with acetone and the filtrate concentrated under reduced pressure. The residue was re-dissolved in ethyl acetate (150 ml) and the organic phase washed with water (2×100 ml). The organic phase was dried over anhydrous $Na_2SO_4$, the drying agent filtered off and washed with ethyl acetate, and the filtrate concentrated under reduced pressure to give an off-white solid (R,S)-2 3.90 g (70%).

Example 4

Synthesis of (R,S)-2

(R,S)-Albuterol (2.39 g, 10,0 mmol) was slurried in 50 cm³ dry acetone in an ice bath. Anhydrous $CuSO_4$ (1.65 g, 10.0 mmol) was added followed by the dropwise addition of $H_2SO_4$ (1.28 ml, 22.0 mmol). After stirring at ca 0° C. for 60 minutes, the reaction mixture was slowly added to 50 cm³ cold aqueous $Na_2CO_3$. The excess acetone was removed under reduced pressure and the resulting aqueous solution extracted three times with an equal volume of ethyl acetate. The combined organic phases were dried ($MgSO_4$) and the solvent removed under reduced pressure to give a crystalline (2.70 g). The product was purified by column chromatography on silica gel with ethyl acetate/petroleum ether (boiling range of 60–80° C.)/triethylamine 50/45/5 to afford the white crystalline product (R,S)-2 (2.65 g, 9,50 mmol, 95%), mp 90–91° C. (acetone).

Characterisation of Isopropylidene Ketal of Albuterol, 2

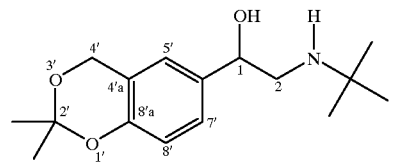

Found C, 68.9; H, 9.3; N, 5.0%;
Requires C, 68.8; H, 9.0; N, 5.0%;
$C_{16}H_{25}NO_3$;
Mass spec.: Requires: M,279 Found: M+,279;
$^1$H-NMR, 200 MHz (CDCl$_3$) δH: 1.08 (9H,s, t-Bu), 1.52 (6H,s, 2×2'-CH$_3$), 2.56 (1H, dd, J11,7 and 9.0 Hz, 2-H), 2.80 (1H, dd, J11.7 and 3.5 Hz, 2-H), 4.51 (1H, dd, J9.0 and 3.5 Hz, 1-H), 4.82 (2H, s, 4'-H$_2$), 6.78 (1H, d, J8.3 Hz, 8'-H), 6.99 (1d, J1.6 Hz, 5'-H), 7.11 (1H, dd, J8.3 and 1.6 Hz, 7'-H);
$^{13}$C-NMR, 200 MHz (CDCl$_3$) δC: 24.6 and 24.8 (2'-CH$_3$), 29.1 (t-Bu-CH$_3$), 50.3 (C-2), 50.3 (t-Bu C-(CH$_3$)$_3$) 61.0 (C4'), 72.0 (C-1), 99.5 (C-2'), 116.8 (C-8), 119.2 (C-4'a), 122.0 (C-5'), 125.7 (C-7'), 134.8 (C-6'), 150.5 (C-8'a).

Determination of the crystal structure of (S)-2 confirmed the formation of the ketal derivative of 1.

Example 5

Synthesis of 2(R)-2:3a Salt (1.90 g, 6.8 mmol) 2 (i.e. (R,S)-2) was dissolved in 15 ml MeOH and the solution heated to reflux. The resolving agent, 3a (1.32 g, 3.5 mmol) was dissolved in 10 ml hot MeOH and transferred to the refluxing solution of 2 with a further 5 ml MeOH. On cooling, a solid cake precipitated from the solution and a further 20 ml MeOH was added. The slurry was refluxed for 10 minutes and was then stirred at room temperature for 2 hours. The solid material was collected by filtration, washed with ethyl acetate and dried to yield 1.10 g salt (70% yield as single enantiomer in 2:1 (R)-2:3a salt; 94% e.e. by HPLC of 2 after extraction).

Figure 3:
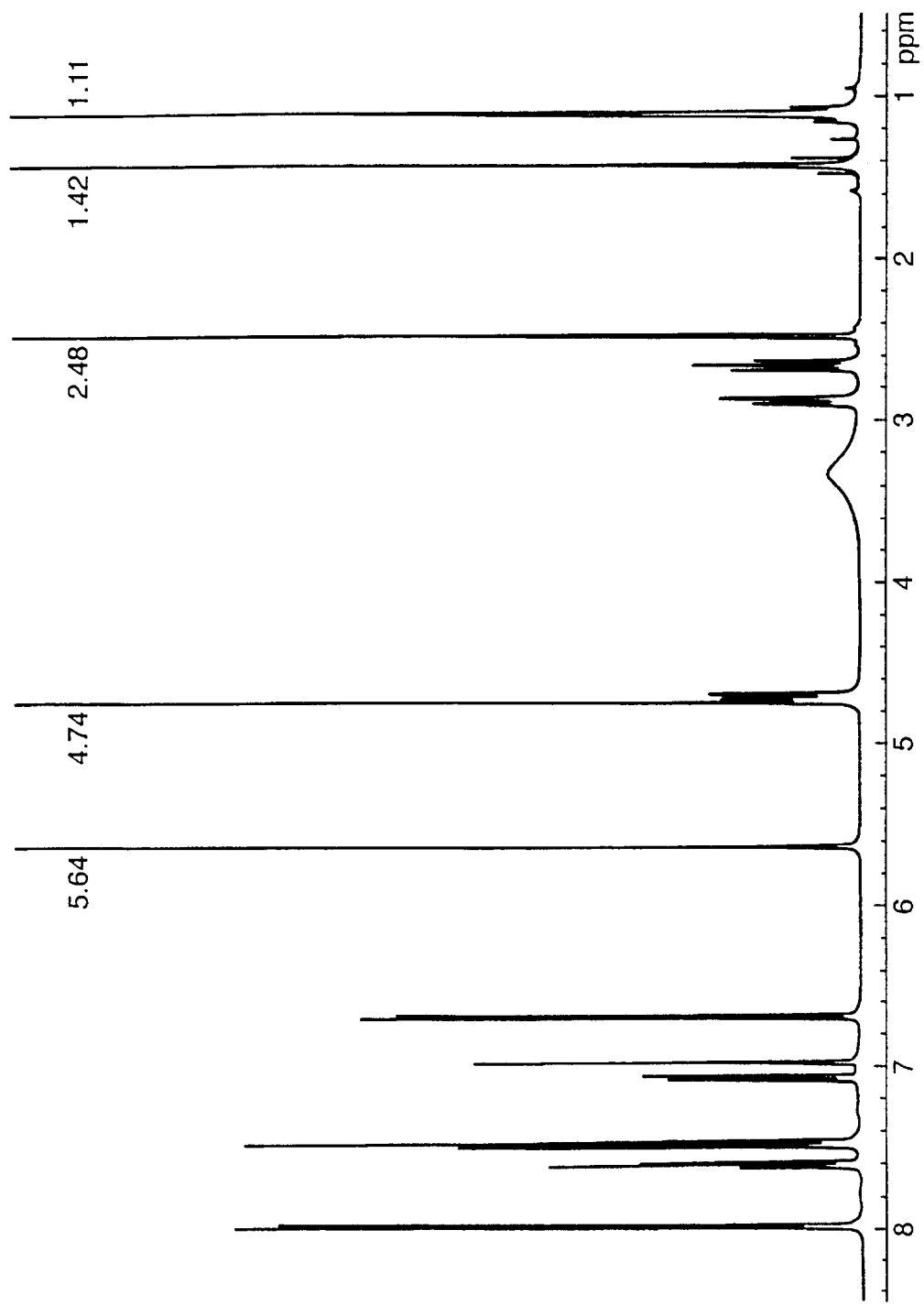
FIG. 3 is a $^1$H-NMR spectrum of 2(R)-2:3a in CDCl$_3$.

The ratio of base: acid in the salt was established by $^1$H-NMR. A spectrum (400 MHz) was run of the salt in DMSO-d$_6$ (See FIG. 3). Integration of the peak at δ1.11 ppm gives 43 integration units and is due to the 9 t-butyl protons on the base. The peak at δ5.64 ppm, due to the 2 methine protons on the acid however, only integrates to give 5 units, indicating that a 2:1 base: acid ratio is present. This is confirmed by the microanalysis results:

Expected: C, 65.5; H, 7.0; N, 3.1%;
Obtained: C, 65.3; H, 7.1; N, 3.0%.

Example 6

Synthesis of 2(R)-2:4a Salt (7.50 g, 27 mmol) 2 (i.e. (R,S)-2) was dissolved in 60 ml MeOH and the solution heated to reflux. 4a (5.3 g, 13.7 mmol) was dissolved in 40 ml hot MeOH and added to the solution of 2. Precipitation of the salt started during the addition and a solid cake was formed. A further 100 ml methanol was added and the slurry refluxed for 10 minutes followed by stirring at room temperature for 2 hours. The precipitate was filtered off, washed with ethyl acetate and dried to afford 5.75 g salt (90% as single enantiomer in a 2:1 base:acid salt; 90% e.e. by HPLC of 2 after extraction).

Figure 4:
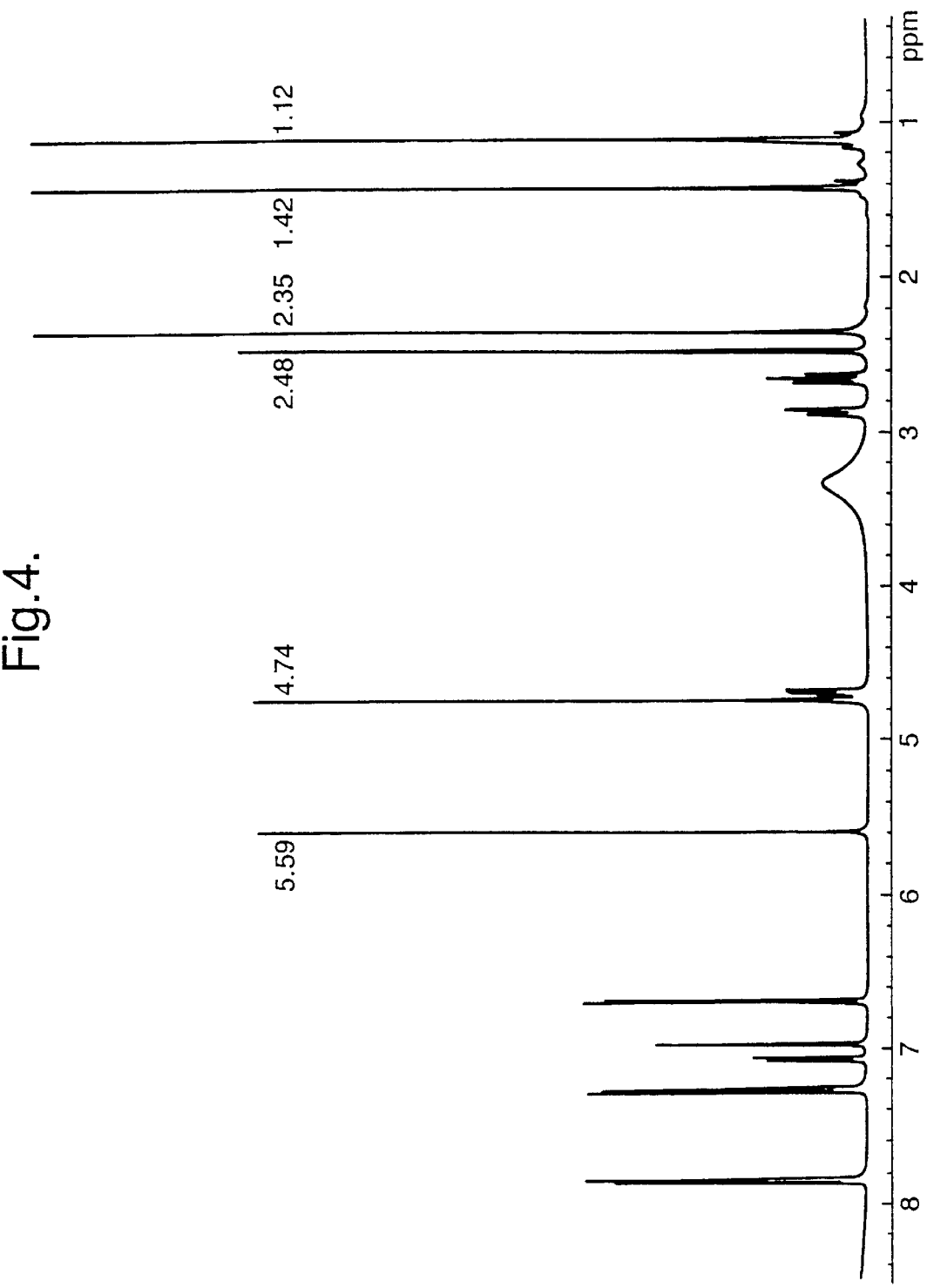
FIG. 4 is a $^1$H-NMR spectrum of 2(R)-2:4a in CDCl$_3$.

The acid: base ratio was established by $^1$H-NMR (400 MHz in DMSO) as above to be 2:1 base:acid (FIG. 4).

The microanalysis results again confirm the NMR findings:

Expected: C, 66.1; H, 7.2; N, 3.0%;
Obtained: C, 65.8; H, 7.3; N, 2.9%;

Example 7

Synthesis of 2(S)-2:3b Salt (1.33 g, 4.8 mmol) 2 (i.e. (R,S)-2) and 3b (0.90 g, 2.5 mmol) were weighed into a flask. 60 ml boiling ethanol was added to achieve dissolution. Precipitation started as soon as dissolution was complete. The solution was left to stand overnight. The solid material was collected by filtration and dried to yield 0.98 g salt (89% as single enantiomer in a 2:1 base:acid salt).

Example 8

Synthesis of 2(S)-2:4b Salt (1.00 g, 3.6 mmol) 2 (i.e. (R,S)-2) and 4b (1.38 g, 3.6 mmol) were weighed into a flask and 75 ml hot methanol added to achieve dissolution. Precipitation started on cooling and the solution was left to stand overnight. The precipitate was filtered off and dried to yield 0.77 g salt (91% as a single enantiomer in a 2:1 base:acid salt).

Example 9

Recovery of (R)-2 from 2(R)-2:3a Salt 0.80 g salt from example 5 was mixed with 100 ml $H_2O$ and 100 ml ethyl acetate. Solid $Na_2CO_3$ was added until pH reached 10. The mixture was stirred vigorously until no solid material remained. The aqueous layer was extracted with a further two portions of ethyl acetate and the combined organic phases dried over $MgSO_4$ and the solvent removed under reduced pressure to yield the white crystalline product (R)-2 (0.46 g, 98%). $^1$H-NMR ($CDCl_3$, 400 MHz) confirmed this to be the expected compound 2 (i.e. (R)-2) by comparison of peaks with the original observed spectrum of 2 (i.e. (R)-2).

Example 10

Synthesis of (R)-2 from (R,S)-2

Resolution of (R,S)-2

Recrystallised (R,S)-2 (17.59 g, 62.97 mmol) was dissolved in MeOH (75 ml) and heated to reflux. To this was added a solution of 4a (12.16 g, 31.40 mmol, 0.5 equiv.) in MeOH (30 ml). During the addition, precipitation of the salt started. The solid cake became unstirrable and a further 40 ml MeOH was added. With time, the cake broke up and stirring was continued at reflux for a total of 7.5 hours. The slurry was stirred for a further 12 hours at room temperature after which time the precipitate was filtered off. Dry yield: 16.36 g (110%).

A portion of the 2(R)-2:4a salt (1.00 g, 1.058 mmol) was slurried in a solution of NaOH (127 mg, 3.174 mmol, 3 equiv.) in water (25 ml). Ethyl acetate (25 ml) was added and the slurry was stirred. After 5 minutes, when some insoluble material was still present, more NaOH (ca 130 mg, ca 3.2 mmol, ca 3 equiv.) was added and the clear phases were separated. The aqueous phase was further extracted with two portions of ethyl acetate (20 ml, 15 ml). The combined organic phases were washed with water (20 ml) and brine (10 ml) and dried over anhydrous $Na_2SO_4$. The drying agent was filtered off, washed with ethyl acetate and the filtrate concentrated under reduced pressure. Dry yield: 0.56 g (95% yield).

$\alpha_D = -12.9°$ (c, 5.6 methanol).

The enantiomeric excess was determined using the chiral HPLC method: 64% ee.

The remaining 2(R)-2:4a salt (15.36 g) was slurried in refluxing MeOH (150 ml, 10 volumes) for 3.5 hours after which time the slurry was left to cool and was stirred for a further 12 hours at room temperature. The precipitate was then filtered off. Dry yield: 12.73 g (83% yield).

The material was re-slurried in refluxing MeOH (150 ml, 11.8 volumes) for 4.5 hours after which time it was allowed to cool and slurried for 65 hours at room temperature. The precipitate was then filtered off. Dry yield 11.59 g (91% yield).

Twice slurried salt (2(R)-2:4a) (10.59 g, 11.21 mmol) was slurried in a solution of NaOH (1.345 g, 33.62 mmol, 3 equiv.) in water (150 ml). Ethyl acetate (150 ml) was added and the slurry stirred vigorously. More NaOH (0.40 g, 10.0 mmol) was added over 10 minutes to effect clear phases. The phases were separated and the aqueous phase was re-extracted with more ethyl acetate (1×75 ml, 1×50 ml). The combined organic phases were washed with water (100 ml) and brine (50 ml). The resulting emulsion was filtered through a sintered glass funnel to facilitate separation of the phases. The organic phase was dried over anhydrous $Na_2SO_4$, the drying agent was filtered off, washed with ethyl acetate (20 ml) and the filtrate was concentrated under reduced pressure to afford 2 (i.e. (R)-2). Dry yield: 5.75 g (92%).

$\alpha_D = -18.6°$ (c 5.7 MeOH)

Chiral HPLC method: 95.6% ee.

Recrystallisation of (R)-2

(R)-2 (6.0 g) was dissolved in hot acetonitrile (ca 20 ml) and the turbid solution was filtered through a 0.45 µl membrane filter. The clear solution was allowed to cool to room temperature whereupon crystallisation occurred. The suspension was cooled in ice for 1.25 hours after which time the crystalline mass was filtered off. Dry yield: 4.0 g (67% yield).

Enantiomeric purity as per chiral HPLC method. 98.6% ee.

Hydrolysis of (R)-2 to (R)-albuterol acetate

Recrystallised (R)-2 (1.00 g, 3.58 mmol) was suspended in acetic acid:water (5:5 ml) and refluxed for 1 hour. The clear and colourless solution was then concentrated under reduced pressure and the residual acetic acid/water was azeotroped with toluene to leave a pale yellow foam. The residue was dissolved in hot MeOH (7 ml) and the solution was allowed to cool to room temperature and then in ice/water. A precipitate formed which was filtered off. Dry yield: 0.58 g (54%).

Enantiomeric purity as per chiral HPLC method: 98.6% ee.

Recrystallised (R)-2 (500 mg, 1.79 mmol) was suspended in a mixture of acetic acid:water (5:5 ml) and heated at 60–65° C. for 3.5 hours. The solution was then concentrated under reduced pressure and the residual acetic acid/water was azeotroped with toluene to leave a pale yellow foam which was recrystallised from MeOH. Dry yield: 0.28 g (52% yield).

Enantiomeric purity as per chiral HPLC method: 98.6% ee.

Example 11

Synthesis of (R,S)-2 from Albuterol Sulfate (R,S)-Albuterol sulfate (2.88 g; 5.00 mmol) was suspended in acetone (60 ml) and slurried at 0° C. to 3° C. in an ice-water bath. Concentrated $H_2SO_4$ (0.80 ml; 15 mmol) was added dropwise to the slurry and the reaction was monitored by TLC until starting material was almost exhausted.

After 5.5 hours, a solution of NaOH (2.00 g; 50.0 mmol) in ca 20 ml MeOH was added in one portion followed by ca 3 g anhydrous $Na_2SO_4$. The slurry was stirred for 10 minutes at 3° C., then filtered through a bed of celite. The solids were washed with acetone and the filtrate was concentrated under vacuum to give an orange oil. The oil crystallised on standing. Ethyl acetate (100 ml) and water (100 ml) were added to dissolve all the material. The phases were separated and the organic layer washed with further water (2×100 ml) and brine (50 ml). The ethyl acetate was evaporated under vacuum to give a light orange solid (2.17 g; 7.78 mmol; 77%).

Example 12

Hydrolysis of (R)-2

Denatured spirits (70 ml) and concentrated $H_2SO_4$ (0.60 ml; 10.9 mmol) were stirred together at ambient temperature (23° C. ). (R)-2 (2.00 g; 7.17 mmol; 97% ee) was added and dissolution occurred rapidly. The reaction was monitored by TLC and completion of hydrolysis was reached within 2 hours. The solution was cooled in an ice bath. Triethylamine (1.82 ml; 13.17 mmol) was then added in two portions and the pH adjusted to 5–6. The solution became turbid during addition of the second portion of triethylamine. The slurry was concentrated under vacuum until ca 15 ml of ethanol remained, chilled in the fridge for 60 hours and filtered. The solids were dried to yield (R)-albuterol sulfate.

Example 13

Hydrolysis of (R)-2

Methanol (71 ml) and concentrated $H_2SO_4$ (0.50 ml; 9.05 mmol) were stirred together at ambient temperature (21° C.). (R)-2 (2.00 g; 7.17 mmol; 97% ee) was added and dissolved rapidly to give a clear, colourless solution. After 1.5 hours the reaction was cooled in an ice bath and a chilled solution of NaOH (0.68 g; 17.0 mmol) in MeOH (ca 10 ml) added whereupon a heavy white precipitate formed. The slurry was stirred for 10 minutes and allowed to warm to ambient temperature. The slurry was filtered three times through celite to obtain a clear, pale yellow filtrate. The filtrate was concentrated under vacuum to yield crude (R)-1 (1.70 g; 7.11 mmol; 99%). The crude material was recrystallised from MeOH to give a fine white powder of (R)-1.

Example 14

Hydrolysis of (S)-2

Methanol (35.5 ml) and concentrated $H_2SO_4$ (0.25 ml, 4.53 mmol) were stirred at 40° C. (S)-2 (1.00 g, 3.58 mmol, ee=91%) was added in one portion and dissolved rapidly. After 1 hour at 40° C. TLC showed no unreacted starting material while chiral HPLC demonstrated 95% completion of the hydrolysis and no change in enantiomeric excess.

A chilled solution of NaOH (0.32 g, 8.00 mmol) in ca 6 ml MeOH was added to the reaction solution. The resulting slurry was stirred in an ice bath for 15 minutes. The solid material was filtered off through celite and the clear filtrate. concentrated under vacuum. A pale yellow oil remained which was redissolved in acetone and concentrated under vacuum to give a foam of crude (S)-1 (0.82 g; 3.44 mmol; 96%).

Example 15

Recycling Enantiomerically Enriched 2 to (R)-2

Racemisation of enantiomerically enriched 2.

(R)-enriched 2 (4.18 g, 15.00 mmol; % (S)-isomer=16% by HPLC) was dissolved in 0.50M $H_2SO_4$ solution (150 ml, 74.7 mmol, 10 equivalents of $H^+$) in a light-protected vessel. The solution was stirred at 57 to 67° C. for 7.5 hours. TLC showed rapid deprotection of the ketal (2) to albuterol (1), the reaction being complete in less than 1 hour. The initial optical rotation was measured as $\alpha_D=-23.3°$ (c=2.8). After 7.5 hours, the solution was cooled to room temperature and optical rotation measured $\alpha_D=-5.0°$ (c=2.8).

The reaction solution was cooled further on ice and a solution of chilled NaOH (6.00 g, 150.0 mmol) in water was added (pH=9.44). The pH was adjusted to 3.42 with 0.5 M $H_2SO_4$. The solvent was then removed under vacuum at 50° C. by azeotropic distillation with toluene, to give a yellow oil mixed with white solids. This material was slurried in ca 70 ml MeOH and the pH adjusted to 9.73 with further NaOH in MeOH. The salts were filtered off through celite to yield a clear orange solution. The methanol was removed under vacuum to give a dark orange oil. The oil was dissolved in acetone and then concentrated under vacuum to give semi-crystalline white solids and some orange oil that solidified on standing (4.19 g; 117%, 43% (S)-isomer by HPLC).

Ketalisation of racemised albuterol

The racemised albuterol (1) (4.09 g, 17.1 mmol) was then slurried in 80 ml acetone in an ice-water bath. Concentrated $H_2SO_4$ (1.89 ml, 34.2 mmol) was added dropwise over 6 minutes. The solution became clear and was stirred at 0–3° C. for 6.5 hours. After 6.5 hours a solution of NaOH (3.00 g, 75.2 mmol) in 30 ml MeOH was added in one portion followed by ca 5 g anhydrous $Na_2SO_4$. The resulting heavy slurry was stirred in an ice bath for 15 minutes. The slurry was filtered through celite and washed with acetone to give a clear yellow filtrate. The solution was concentrated under vacuum to give a dark orange oil. This was taken up in 100 ml ethyl acetate and 100 ml water was added. The phases were separated with the addition of brine. The organic phase was washed twice with water (80 ml, 60 ml), 30 ml brine, dried with anhydrous $Na_2SO_4$ and concentrated under vacuum to yield an orange oil of crude (R,S)-2 that solidified on standing. (3.07 g, 11.0 mmol, 65%, 45% (S)-isomer by HPLC).

Resolution of racemised albuterol ketal

Crude (R,S)-2 (ca 2.68 g) was dissolved in 20 ml methanol. The clear solution was heated to reflux. A hot solution of compound 4a (1.86 g, 4.80 mmol) in 15 ml MeOH was added. The solution was refluxed for 15 minutes then removed from heat and stirred at room temperature for 70 hours.

The solids were filtered off, washed with ethyl acetate and dried to yield 2(R)-2:4a salt (1.66 g; 1.76 mmol; 73%; 94.4% ee by HPLC).

2(R)-2:4a (1.59 g, 1.68 mmol) was slurried in 16 ml MeOH and refluxed for 3 hours. The slurry was stirred overnight at room temperature (18 hours) then filtered. The solids were washed with ethyl acetate and dried to yield 2(R)-2:4a (1.43 g; 1.51 mmol; 90%; 96.0% ee by HPLC).

2(R)-2:4a; (1.37 g, 1.44 mmol) was then further slurried in 14 ml MeOH and refluxed for 4 hours. The slurry was stirred overnight at room temperature (18 hours) then filtered. The salt was washed with ethyl acetate and dried to yield 2(R)-2:4a (1.16 g; 1.23 mmol; 85%).

Hydrolysis of (R)-2:tartrate salt

The twice slurried 2(R)-2:4a salt (1.14 g, 1.20 mmol) was slurried in aqueous NaOH (148 mg, 3.70 mmol, 3 equivalents) in 25 ml $H_2O$ and ethyl acetate (25 ml) was added. The slurry was stirred for 10 minutes and additional NaOH (145 mg, 3.63 mmol, 3 equivalents) in ca 2 ml $H_2O$ was added whereupon the phases cleared rapidly. The phases were separated and the aqueous phase extracted twice with ethyl acetate (20 ml, 10 ml). The combined organic phases were washed with water (20 ml) and brine (15 ml) and dried over anhydrous $Na_2SO_4$. The filtrate was concentrated under vacuum to give white crystals of (R)-2 (0.63 g, 2.26 mmol, 94%; 97.3% ee by HPLC).

Example 16

(R,S)-2 from S-enriched 2

S-enriched 2 (4.18 g; 15.0 mmol) was dissolved in dilute $H_2SO_4$ (150 ml; 75 mmol; 0.50 M) at ambient temperature. Upon complete dissolution, the optical rotation of the solution was measured: $\alpha^D=+17.2°$ (c=2.8).

The reaction solution was heated to between 50 and 68° C. for 7 h. The optical rotation of the solution was remeasured: $\alpha^D=+2.1°$ (c=2.8). The solution was stored in the fridge overnight at 5° C.

A chilled solution of NaOH (5.00 g; 125 mmol) in ca 30 ml water was added to the reaction solution. Further NaOH and $H_2SO_4$ were added to adjust the pH to 3.27. The water was removed under vacuum to leave a white crystalline solid and a yellow oil. The last traces of water were removed by azeotropic distillation with toluene. Crude yield: 13.9 g.

The racemised albuterol sulfate, together with the salts of neutralisation were slurried in acetone (80 ml) and chilled in an ice bath. Concentrated $H_2SO_4$ (1.24 ml; 22.5 mmol) was added dropwise to the slurry. The racemised albuterol sulfate dissolved to give a clear yellow solution, but $Na_2SO_4$ salts remained suspended.

The reaction was stirred in an ice bath and monitored by TLC. After 2 hours, the starting material was almost exhausted and a chilled solution of NaOH (1.80 g; 45 mmol) in MeOH (ca 20 ml) was added. A heavy precipitate resulted and the slurry was stirred on ice for 5 minutes. The slurry was filtered through celite. The filtrate was concentrated under vacuum and the residue was taken up in ethyl acetate (200 ml) and water (300 ml). The solvent was removed under vacuum as the phase separation was not clear. The crude reaction product was dissolved in ethyl acetate (100 ml) and water (100 ml) and the phases separated. The organic layer was washed with purified water (80 ml, 60 ml) and 25 ml brine. The aqueous phase was re-extracted twice with ethyl acetate (100 ml, 50 ml), the organic phases combined and dried over anhydrous $Na_2SO_4$. The drying agent was filtered off, washed with ethyl acetate and the filtrate was concentrated under vacuum to yield a yellow oil that crystallised with drying to give (R,S)-2 (1.06 g; 3.80 mmol; 25% yield from S-enriched 2).

REFERENCES

1 H. W. Kelly and S. Murphy, (1992), Annu. Pharmacother., 26, 81–91.
2 D. Siegel, D. Sheppard, H. Gelb and P. F. Weinberg, (1985), Am. Rev. Respir. Dis., 132,283–286.
3 S. Godfrey and P. Konig, (1976), Thorax, 31, 137–143.
4 D. Hartley and D. Middlemiss, (1971), J. Med. Chem., 14, 895–896.
5 Y. Gao and C. M. Zepp, U.S. Pat. No. 5,399,765, (Mar. 21, 1995).
6 Y. Gao and C. M. Zepp, U.S. Pat. No. 5,545,745, (Aug. 13, 1996).
7 Y. Gao, Y. Hong and C. M. Zepp, U.S. Pat. No. 5,442,118, (Aug. 15, 1995).
8 D. P. Venter, (1991), Tetrahedron, 47(27), 5019–5024.

What is claimed is:

1. A process for the preparation of 2-(N-t-butylamino)-1-(2,2-dimethyl-1,3-benzodioxin-6-yl) ethanol (2), which process includes the steps of:
   (1) suspending albuterol (1) or a salt thereof, in acetone;
   (2) adding to the mixture of step (1) a suitable acid with stirring to form the compound of the formula (2);
   (3) adding to the mixture of step (2) a suitable aqueous or non-aqueous basic solution; and
   (4) recovering the compound of the formula (2) from the mixture of step (3).

2. A process for the optical resolution of a mixture of enantiomers of 2-(N-t-butylamino)-1-(2,2-dimethyl-1,3-benzodioxin-6-yl) ethanol (2) into its (R)-isomer designated (R)-2 and its (S)-isomer designated (S)-2, which process includes the steps of:
   (i) reacting the mixture of enantiomers of the compound of the formula (2), dissolved in a suitable solvent, with an enantiopure tartaric acid derivative;
   (ii) precipitating selectively out of the solution of step (i) a compound of the formula:
       (R)-2:tartaric acid derivative salt or
       (S)-2:tartaric acid derivative salt;
   (iii) suspending the (R)-2:tartaric acid derivative salt or the (S)-2:tartaric acid derivative salt in a suitable organic solvent and stirring to improve optical purity, and then recovering the (R)-2:tartaric acid derivative salt or the (S)-2:tartaric acid derivative salt by filtration;
   (iv) adding the (R)-2:tartaric acid derivative salt or the (S)-2:tartaric acid derivative salt from step (iii) to a mixture of an aqueous solution of a base and a suitable organic solvent; and
   (v) recovering the compound (R)-2 or the compound (S)-2 from the organic phase of step (iv).

3. A process according to claim 2 wherein in step (i) the solvent is a lower alcohol.

4. A process according to claim 2 or claim 3 wherein in step (i) the tartaric acid derivative is selected from the group consisting of (2S,3S)-(+)-di-O-benzoyl tartaric acid (3a), (2S,3S)-(+)-di-O-(p-toluoyl)-tartaric acid (4a), (2R,3R)-(−)-di-O-benzoyl tartaric acid (3b), and (2R,3R)-(−)-di-O-(p-toluoyl)-tartaric acid (4b).

5. A process for the hydrolysis of 2-(N-t-butylamino)-1-(2,2-dimethyl-1,3-benzodioxin-6-yl) ethanol (2) to give albuterol (1) either as the free base or as a salt, which process includes the steps of:
   (a) dissolving the compound of the formula (2), either enantiomerically enriched or as the racemic mixture, in an excess of an acid, and water or any suitable organic solvent, to hydrolyse the compound of the formula (2); and (b) recovering the compound of the formula (1) either as a salt of the acid used in step (a), or as the free base.

6. A process for resolving the enantiomers of albuterol (1) into the (R)-enantiomer designated (R)-1 and the (S)-enantiomer designated (S)-1, which process includes the steps of:

(i) suspending albuterol (1) or a salt thereof, in acetone;

(ii) adding to the mixture of step (i) a suitable acid with stirring to form 2-(N-t-butylamino)-1-(2,2-dimethyl-1,3-benzodioxin-6-yl) ethanol (2);

(iii) adding to the mixture of step (ii) a suitable aqueous or non-aqueous basic solution;

(iv) recovering the compound of the formula (2) as a mixture of enantiomers designated (R)-2 and (S)-2;

(v) reacting the mixture of enantiomers of the compound of the formula (2) from step (iv), dissolved in a suitable solvent, with an enantiopure tartaric acid derivative;

(vi) precipitating selectively out of the solution of step (v) a compound of the formula:
(R)-2:tartaric acid derivative salt or
(S)-2:tartaric acid derivative salt;

(vii) suspending the (R)-2:tartaric acid derivative salt or the (S)-2: tartaric acid derivative salt from step (vi) in a suitable organic solvent and stirring to improve optical purity, and then recovering the (R)-2:tartaric acid derivative salt or the (S)-2:tartaric acid derivative salt by filtration;

(viii) adding the (R)-2:tartaric acid derivative salt or the (S)-2:tartaric acid derivative salt from step (vii) to a mixture of an aqueous solution of a base and a suitable organic solvent;

(ix) recovering the compound (R)-2 or the compound (S)-2 from the organic phase of step (viii);

(x) dissolving the compound (R)-2 or the compound (S)-2 from step (ix) in an excess of an acid, and water or any other suitable organic solvent, to hydrolyse the compound (R)-2 or the compound (S)-2; and (xi) recovering the compound (R)-1 or the compound (S)-1 either as a salt or as the free base.

7. A process according to claim 6 for the recovery of the compound of the formula (R)-1.

8. A process according to claim 6 or claim 7 wherein in step (v) the enantiopure tartaric acid derivative is selected from the group consisting of (2S,3S)-(+)-di-O-benzoyl tartaric acid (3a), (2S,3S)-(+)-di-O-(p-toluoyl)-tartaric acid (4a), (2R,3R)-(−)-di-O-benzoyl tartaric acid (3b), and (2R,3R)-(−)-di-O-(p-toluoyl)-tartaric acid (4b).

9. A process for the racemisation of optically enriched albuterol (1) or a salt thereof or optically enriched 2-(N-t-butylamino)-1-(2,2-dimethyl-1,3-benzodioxin-6-yl) ethanol (2) or a salt thereof to give a mixture of enantiomers of the compound of the formula (1), which process includes the steps of:

(A) dissolving optically enriched compound of the formula (1) or a salt thereof, or optically enriched compound of the formula (2), in a solution of an excess of a suitable acid and a suitable solvent to produce racemised compound of the formula (1);

(B) adding to the solution of step (A) a suitable aqueous or non-aqueous base; and (C) recovering a mixture of enantiomers of the compound of the formula (1) from the mixture of step (B).

10. A process according to claim 9 wherein in step (A) the solvent is selected from the group consisting of water, a lower alcohol, acetonitrile and tetrahydrofuran, or a mixture of water and a lower alcohol, acetonitrile or tetrahydrofuran.

* * * * *